US008802410B2

(12) United States Patent
Käck et al.

(10) Patent No.: US 8,802,410 B2
(45) Date of Patent: Aug. 12, 2014

(54) MASS-SENSITIVE CHEMICAL SENSOR HAVING A BINDING SURFACE FOR LIGANDS

(75) Inventors: Camilla Käck, Sollentuna (SE); Julien Saint-Guirons, Solna (SE); Björn Ingemarsson, Täby (SE); Kerstin Lundell, Stockholm (SE)

(73) Assignee: Attana AB, Stockholm (SE)

(*) Notice: Subject to any disclaimer, the term of this patent is extended or adjusted under 35 U.S.C. 154(b) by 253 days.

(21) Appl. No.: 12/728,212

(22) Filed: Mar. 20, 2010

(65) Prior Publication Data

US 2012/0198920 A1    Aug. 9, 2012

(30) Foreign Application Priority Data

Mar. 20, 2009 (GB) .................................. 0904861.2
Dec. 17, 2009 (GB) .................................. 0922100.3

(51) Int. Cl.
  *C12N 11/06*    (2006.01)
  *G01N 33/543*   (2006.01)
  *G01N 29/02*    (2006.01)
  *G01N 29/036*   (2006.01)

(52) U.S. Cl.
  CPC .......... *G01N 33/54373* (2013.01); *C12N 11/06* (2013.01); *G01N 29/022* (2013.01); *G01N 29/036* (2013.01); *G01N 2291/0255* (2013.01); *G01N 2291/0256* (2013.01); *G01N 2291/0426* (2013.01)
  USPC .......................................... 435/181; 435/180

(58) Field of Classification Search
  USPC ......................................... 435/174, 180, 181
  See application file for complete search history.

(56) References Cited

U.S. PATENT DOCUMENTS

| | | | |
|---|---|---|---|
| 6,289,717 B1* | 9/2001 | Thundat et al. ................. 73/23.2 |
| 6,325,904 B1* | 12/2001 | Peeters ......................... 257/414 |
| 6,977,149 B2* | 12/2005 | Kajiyama et al. ............ 435/6.19 |
| 7,087,658 B2* | 8/2006 | Swan et al. ..................... 522/36 |
| 7,288,404 B2* | 10/2007 | Vafai et al. ................. 435/287.1 |
| 7,560,070 B1* | 7/2009 | Baller et al. ..................... 422/50 |
| 7,765,854 B2* | 8/2010 | Schilowitz et al. .......... 73/64.53 |
| 8,329,452 B2* | 12/2012 | Roukes et al. ............. 435/287.2 |
| 8,434,161 B1* | 4/2013 | Adams et al. .................... 850/56 |
| 8,481,335 B2* | 7/2013 | Shih et al. ....................... 436/524 |
| 8,511,163 B2* | 8/2013 | Mutharasan et al. ........... 73/579 |
| 2003/0008335 A1 | 1/2003 | Marx et al. |
| 2004/0029108 A1* | 2/2004 | Bottomley et al. ............... 435/5 |

(Continued)

FOREIGN PATENT DOCUMENTS

| WO | 01/25780    | 4/2001 |
| WO | 2008/132487 | 11/2008 |
| WO | 2008/136787 | 11/2008 |

OTHER PUBLICATIONS

Hendrick et al., "Adhesion, growth and detachment of cells on modified polystyrene surface", Cytotechnology, No. 36, pp. 49-53, 2001.*

(Continued)

*Primary Examiner* — David A Rogers
(74) *Attorney, Agent, or Firm* — Banner & Witcoff, Ltd.

(57) ABSTRACT

There is disclosed an analytical method and a sensor suitable for carrying out the method. More specifically, there is disclosed a method for preparing a mass sensitive chemical sensor capable of detecting binding analyte species to a surface comprising cells.

8 Claims, 6 Drawing Sheets

(56) References Cited

U.S. PATENT DOCUMENTS

| | | | |
|---|---|---|---|
| 2004/0235198 | A1 | 11/2004 | Marx et al. |
| 2006/0024813 | A1 | 2/2006 | Warthoe |
| 2006/0191320 | A1* | 8/2006 | Pinnaduwage et al. ...... 73/24.06 |
| 2007/0218453 | A1* | 9/2007 | Tanizawa et al. .................. 435/4 |
| 2007/0237676 | A1* | 10/2007 | Colton et al. ................. 422/68.1 |
| 2010/0087011 | A1* | 4/2010 | Cooper .......................... 436/501 |
| 2010/0227372 | A1* | 9/2010 | Bilek et al. ..................... 435/180 |
| 2010/0304427 | A1* | 12/2010 | Faris et al. ....................... 435/29 |

OTHER PUBLICATIONS

Fohlerová et al., "Adhesion of eukaryotic cell lines on the gold surface modified with extracellular matrix proteins monitored by the piezoelectric sensor", Biosensors and Bioelectronics, Sep. 18, 2006.*

O'Brien et al., "Immunosensing Platforms Using Spontaneously Adsorbed Antibody Fragments on Gold", Analytical Chemistry, vol. 72, No. 4, Feb. 15, 2000.*

Feng et al., "Tailored interfaces for biosensors and cell-surface interaction studies via activation and derivatization of polystyrene-block-poly(tert-butyl acrylate) thin films," European Polymer Journal 43 (2007) pp. 2177-2190.

Stoker, "Methods for identifying extracellular ligands of RPTPs," Methods 35 (2005) pp. 80-89.

Lindegren et al., "Determining Therapeutic Agent Receptor Target Interactions with the Assistance of a Novel Bisensor Application," conference presentation at 'Discovery Summit' in Monaco in Mar. 2009, pp. 23-31.

Barbee et al., "The Study of a Cell-Based TSM Piezoelectric Sensor," 2002 IEEE International Frequency Control Symposium and PDA Exhibition, pp. 260-267.

Chabot et al., "Biosensing based on surface plasmon resonance and living cells," Biosensors and Bielectronics 24 (2009), pp. 1667-1673.

Chou et al, "Detecting cells on the surface of a silver electrode quartz crystal microbalance using plasma treatment and graft polymerization," Collids and Surfaces B: Biointerfaces 73 (2009), pp. 244-249.

Yanase et al., "The SPR signal in living cells reflects changes other than the area of adhesion and the formation of cell constructions," Biosensors and Bioelectronics 22 (2007), pp. 1081-1086.

Yanase et al., "Living cell positioning on the surface of gold film for SPR analysis," Biosensors and Bioelectronics 23 (2007), pp. 562-567.

Blonder et al., "Photochemically-Activated electrodes: application in design of reversible immunosensors and antibody patterned interfaces," Biosensors and Bioelectronics, vol. 12, No. 7, pp. 627-644, (1997).

Gizeli et al., "Acoustic transducers," Book Biomolecular Sensors, Part III, Chapter 7, pp. 176-206, published 2002.

Marx et al., "A comparative study of the cytoskeleton binding drugs nocodazole and taxol with a mammalian cell quartz crystal microbalance biosensor: Different dynamic responses and energy dissipation effects," Analytical Bichemistry 361 (2007), pp. 77-92.

Fung et al., "Self-Assembled Monolayers as the Coating in a Quartz Piezoelectric Cystal Immunosensor to Detect Salmonella in Aqueous Solution," Analytical Chemistry 73 (2001), pp. 5302-5309.

Cooper et al., "Acoustic Anaysis of Molecular Interactions," J. Mol. Recognit. 2007; 20; pp. 166-172.

Myszka, "Improving biosensor analysis," Journal of Molecular Recognition, 1999, 12:279-284.

Morton et al., "Kinetic Analysis of Macromolecular Interactions Using Surface Plasmon Resonance Biosensors," Methods in Enzymology, vol. 295, 1998, pp. 268-294.

Brock et al., "Comparison of Fixation Protocols for Adherent Cultured Cells Applied to a GFP Fusion Protein of the Epidermal Growth Factor Receptor," Cytometry 35:353-362, 1999.

* cited by examiner

MASS-SENSITIVE CHEMICAL SENSOR HAVING A BINDING SURFACE FOR LIGANDS

TECHNICAL FIELD

The present disclosure provides an analytical method and a sensor suitable for carrying out the method. In particular, though not exclusively, to the disclosure provides a method for preparing a mass sensitive chemical sensor capable of detecting binding analyte species to a surface comprising cells.

CROSS REFERENCE TO RELATED APPLICATIONS

This patent application claims priority from Great Britain patent application 0922100.3 filed on 17 Dec. 2009, which is a continuation-in-part from Great Britain patent application 0904861.2 filed on 20 Mar. 2009.

BACKGROUND

A mass-sensitive chemical sensor can be defined as any device that allows for measurement of a property that scales proportionally to mass associated with or bound to a sensing surface of that device. Several such sensor techniques can be utilised, such as evanescent wave-based sensors, e.g. surface plasmon resonance (SPR, which is capable of registering mass changes by the associated change in refractive index at the surface), optical waveguides (also dependent on refractive index changes associated with mass binding events), optical diffraction, optical interference, ellipsometry and acoustic wave devices (for example quartz crystal microbalances (QCMs)). These sensor approaches are well established in the art (see, for example, *Biomolecular Sensors*, Gizeli and Lowe. Taylor and Francis, London; 2002) and these types of instruments can be used for studies of chemical reactions in situ and for detection of certain molecules in a sample.

A QCM system utilizes the piezoelectric effect of a quartz crystal. In such a system a quartz crystal that is placed between two electrodes, which are connected to an AC-potential, begins to oscillate if the frequency of the AC-potential is close to the resonance frequency of the oscillation mode for the quartz crystal. The resonance frequency of the quartz crystal is a function of many parameters, such as temperature, pressure, cut angle of the crystal, mechanical stress and thickness of the crystal. The resonance frequency is inversely proportional to the thickness of the crystal.

Typical resonance frequencies used in liquid applications range from 1 MHz to 50 MHz. The crystal is normally AT-cut with a circular or square shape with a diameter of approximately 5-10 mm. The electrodes (driving and counter electrodes) are normally of gold on both sides, but other metals are not unusual. The electrodes are very thin compared to the quartz crystal plate and can therefore be considered as part of the crystal plate. When material is added to or removed from one of the electrodes, it becomes thicker or thinner, i.e. the associated weight of the electrode changes. As a consequence of the mass change of the electrode, the resonance frequency of the crystal plate will either decrease or increase and hence the change of resonance frequency can be measured to detect the mass change of the electrode. The mass resolution of a QCM system can be as low as 1 pg/cm$^2$, corresponding to less than 1% of a monolayer of hydrogen.

A typical QCM piezoelectric sensor instrument comprises a sensor element, a sample insertion unit, equipment for determining the piezoelectric properties (including the oscillation frequencies) of a quartz crystal, and signal presentation equipment and buffer and waste containers (other than the sensor element, these items may be referred to as the 'associated apparatus' of the sensor instrument). A sample, which can contain any chemical substance of interest, is introduced into the sensor element by the sample insertion unit. The sensor element contains a piezoelectric resonator (the QCM sensor), a sample chamber, flow channels to and from the chamber and an oscillating circuit. The sample induces an interaction with the piezoelectric sensor surface, which can in turn be observed by monitoring the oscillating characteristics of the crystal plate, e.g. by measuring changes in the piezoelectric resonator frequency. The crystal plate is provided with electrical contact areas for the driving and counter electrodes on its surface, such contact areas being connectable to a signal source (e.g. an alternating voltage source) as well as to a measurement device. For measuring, the piezoelectric crystal plate is on one side brought into contact with the fluid (e.g. liquid) sample to be examined. The crystal responds to the accumulation of the mass of the substance to be detected or to a change in the physical properties of the sample by altering its resonance frequency and/or oscillation amplitude.

Piezoelectric sensors can be used for analysis of the viscosity of a liquid sample and are particularly suitable for studying chemical and biochemical interactions. Ha piezoelectric sensor is to be used for the latter purpose, the electrode that is to be exposed to the sample is provided with a specific surface coating, which will interact with the sample. A review of the types of interactions which can be studied using QCM sensors is provided by Cooper and Singleton (*J. Mol. Recognit.*, 2007, 20, 154). Regardless of the type of chemical sensor, common surface coating approaches include self-assembled monolayers (e.g. alkanethiols adsorbed onto gold) and/or polymeric matrices, each of which may bear functional groups which may be used for immobilising a first chemical species of interest. Typically, the immobilised first chemical species is a small organic molecule or an antibody. The sensor bearing the first chemical species is then brought into contact with a dispersion of a second chemical species or a cell and the binding of the second chemical species or cell to the first chemical species is monitored by means of the resultant change in mass at the sensing surface. Fung and Wong (*Anal. Chem.* 2001, 73, 5302) describe the use of such an approach to detect *Salmonella* cells in a liquid dispersion, and other similar studies are described by Cooper and Singleton (see above).

A more challenging approach is to employ cells as the immobilised, first species in the chemical sensor. A few studies have achieved this, although the reported methods employ live cells and do not analyse the binding interaction per se; rather these methods use biosensor techniques to monitor post-binding morphological or other changes in the cells (see Marx et al., *Anal. Biochem.*, 2007, 361, 77). Such methods are of little or no use for accurately monitoring the binding interaction, due to interference in the detected signal from the cellular changes following the binding event.

The prior art does not describe or suggest a method for preparing a mass sensitive chemical sensor having immobilised cells and which is suitable for accurately detecting and monitoring a binding interaction between the cells and an analyte ligand.

SUMMARY

In accordance with a first aspect of the present invention, there is provided a mass-sensitive chemical sensor, the chemical sensor having inactivated cells adhered to a sensing surface thereof and being suitable for detection of an interaction between an analyte ligand and the adhered, inactive cells by means of the change in mass at the sensor surface due to binding of analyte ligand to the cells, wherein the sensor is provided with, or forms part of, a flow cell. In a preferred embodiment, the cells are fixed.

In certain embodiments of the first aspect, the mass-sensitive chemical sensor is prepared by a method comprising the steps of: contacting a suspension containing cells with the sensing surface of a sensor element; allowing the cells to adhere to and potentially grow on the sensing surface; and, after a suitable period of time, treating the adhered cells so as to render them inactive.

The mass-sensitive chemical sensor of the present invention is able to accurately detect and monitor, potentially in real-time, the binding event per se between analyte ligands and structures on the surfaces of cells. Unlike sensors prepared by prior art methods, the signal produced by the sensor of the present invention relates more directly to the mass of material bound at the sensing surface, with interference due to cell growth and/or morphological changes minimised. In addition, by using fixed cells (where the fixing may be achieved by chemical or physical means, as described in more detail below), the cells are more resistant to any shear forces which arise in the flow cell during use and which would otherwise pose the risk of damage to or stripping of cells from the sensor surface. The term 'inactive' as used herein in relation to the cells is intended to mean that the normal biochemistry of the cells is substantially arrested, such that the cells are substantially no longer capable of growth, division, movement and/or morphological changes.

In accordance with a second aspect, the present invention also provides a method of preparing a mass-sensitive chemical sensor capable of detecting an interaction between an analyte ligand and immobilised cells, the method comprising the steps of: contacting a suspension containing cells with the sensing surface of a sensor element; allowing the cells to adhere to and potentially grow on the sensing surface; and, after a suitable period of time, treating the adhered cells so as to render them inactive.

The method of the second aspect is capable of producing a mass-sensitive chemical sensor which is able to accurately detect and monitor, potentially in real-time, the binding event per se between analyte ligands and structures on the surfaces of cells, as with the sensor of the first aspect. Unlike sensors prepared by prior art methods, the signal produced by the sensor prepared by the present method relates more directly to the mass of material bound at the sensing surface, as explained above.

In a preferred embodiment, the method includes the additional step of integrating the sensor into a flow cell, such that the sensor is provided with, or forms part of, a flow cell. The integration of the sensor into a flow cell may occur at any stage of the method, i.e. before the sensor is contacted with the cells; before, during or after the cells have adhered to and potentially grown on the sensing surface; or before, during or after treatment of the cells to render them inactive.

The flow cell to be used or formed in accordance with the present invention should be one which is preferably adapted for the determination of kinetic rate parameters of the studied interactions. The flow cell should be made of biologically compatible material, preferably selected from, but not limited to, polyoxymethylene, polymethylmethacrylate, polyvinyl chloride and injection-moldable thermoplastics, such as polystyrene or acrylonitrile-butadiene-styrene. The dimensions of the flow cell should be suitable for determination of kinetic rate parameters for molecular interactions, i.e. the flow characteristics should allow for maintenance of the bulk solution concentration of the analyte ligand at, or very close to, the surface with immobilized cells, without substantial diffusion limitation of the analyte ligand to the target molecule on the cell surface. The preferred height of the flow cell should be 50 μm or less (measured from the sensor surface, to the ceiling of the flow cell). Suitable flow cells are described, for example, in PCT/GB2008/001515 (WO 2008/132487).

The suspension containing the cells preferably contains a cell growth medium. Suitable cell growth media for a variety of cells are well known to the skilled person, and the prior art is replete with information concerning preferred and essential constituents of media for culturing the majority of prokaryotic and eukaryotic cells. Preferred media contain serum proteins. It is believed, although the inventors do not wish to be bound by this belief, that the serum proteins present in such growth media adsorb to the sensing surface before (or, less likely, simultaneously with) the cells; the adsorbed proteins then provide a surface having motifs which can be recognised by cell surface components of the cells, thereby enhancing the adhesion of the cells on or near the sensing surface. In certain preferred embodiments of the method, the cell suspension also contains extracellular matrix proteins of relevance to the cells concerned. Such matrix proteins, which vary to a degree depending on the cell type concerned but which, again, can be determined by reference to standard laboratory textbooks, aid cell adhesion by providing additional motifs for recognition and binding by cell surface components. In some embodiments, a protein-covered sensor surface may be used, or the sensing surface may be pre-conditioned by bringing it into contact with a solution of serum proteins and/or extracellular matrix proteins so as to allow adsorption thereof to the surface; in such cases a serum-free cell suspension may readily be used.

In certain embodiments of the first and second aspects, the cells are eukaryotic. In particular, the cells may be animal cells, such as mammalian cells, in particular human cells.

In particular embodiments, the sensing surface is modified, prior to contact with the cell-containing suspension, so as to increase the surface energy and thereby enhance the adhesion of serum proteins and/or cells thereto.

A variety of materials may form the sensing surface of the sensor element of the first aspect, or the sensing surface of the sensor element into contact with which the cell suspension is brought in the second aspect. In some instances, a non-treated metal sensor surface may be used, e.g. a gold electrode of a QCM, or the noble metal surface of an SPR biosensor, or a glass surface, such as may be found in some optical waveguide-based devices. In many embodiments, however, it may be desirable to modify the surface, either by chemical or physical treatment, to increase the rate and/or extent of serum protein and/or cell adsorption thereto. Chemical treatments include the adsorption of polar, hydrophilic and or charged species to the surface (e.g. polyamino acids, such as polylysine; or serum and/or extracellular matrix proteins, as mentioned above, in which case particular recognisable biochemical motifs may play a role in cell adhesion, in addition to any effects on surface polarity etc.). Physical treatments include the use of plasma bombardment or electromagnetic radiation of an appropriate type to cause modification of the surface chemistry of the sensing surface. Such an approach may be particularly useful in the case of otherwise hydrophobic surfaces, such as certain polymer-coated surfaces. In any event, the suitability of the surface for adhesion of cells, and the effects of any modification thereof, can readily be determined by coupling the sensor with the associated apparatus of a sensor instrument, then determining, by means of the change in signal from the sensor, whether and to what extent serum proteins and/or cells brought into contact with the sensing surface adhere. Alternatively or in addition, microscopy may be used to monitor the adhesion of cells to the sensing surface. A sensing surface may be optimised in this way and then used to even greater effect in the method of the invention.

In many cases, the sensing surface, prior to cell immobilisation, has a contact angle of 10 to 90 degrees, preferably 20 to 80 degrees and more preferably 30 to 70 degrees. A contact angle of around 60 degrees may be particularly preferred. Contact angle may be determined by methods standard in the art and, as used herein, refers to a contact angle with high purity water. In certain embodiments of the first and second aspects, the sensing surface is provided with a polymeric coating into contact with which the cell-containing suspension is brought. Such a polymeric coating may comprise a polystyrene. Polymeric coating of mass sensitive chemical sensors is a common approach and allows flexibility in terms of what can subsequently be coupled to the sensing surface. Polystyrene is a common surface used for culturing of cells and hence is particularly useful for the present method. Due to its hydrophobicity, however, the polystyrene coating is preferably modified by plasma bombardment or electromagnetic radiation treatment. UV treatment is particularly preferred. The polymeric coating (e.g. polystyrene) may be prepared by spin-coating of the sensor element with a polymer solution. The polymeric coating may be brought into contact with a dispersion of serum and/or extracellular matrix proteins to allow adsorption thereof prior to bringing the sensor into contact with the cell suspension.

Prior to inactivation of the adhered cells, a period of growth of the cells on the sensing surface may usefully be allowed. Any damage or disturbance to the cells which has occurred during suspension culture can then be attenuated. The 'suitable period of time' referred to above may be determined according to the needs and objectives of the experiment, and the cell type employed, and this period may readily be assessed by trial and error. In particular, many cells adopt a spherical morphology in suspension, whereas adhesion to a surface involves a degree of spreading and flattening of the cells. In terms of the phase of growth at which to harvest the cells for seeding onto the surface of the sensor, this should ideally be during the exponential phase of growth—the cells express receptors more abundantly during this phase.

Treatment of the cells to render them inactive may be achieved by physical means (e.g. maintaining the cells at reduced temperature (e.g. 2-8 deg C.), snap freezing, or heat treatment under reduced pressure; see www.denator.com) or, more preferably, by chemical means (e.g. toxin treatment, or chemical cross-linking). In preferred embodiments, inactivity of the adhered cells is achieved by fixing the cells, either by physical means or, more preferably, by chemical means. Chemical means include both organic solvent-based methods or, more preferably, cross-linking methods. Organic solvent based methods typically work by removing lipids and water from the cells and precipitate cellular proteins, whereas cross-linking reagents form intermolecular bridges between surface components of cells. Solvent based methods include the use of acetone, methanol and/or ethanol, typically at approximately −20 deg C. Cross-linking approaches may employ, for example, formalin, formaldehyde or paraformaldehyde, optionally in conjunction with a surfactant and/or methanol. A number of alternative fixation protocols are also described by Brock et al. (*Cytometry*, 1999, 35, 353).

Fixing of the cells on the sensor surface prevents further growth, migration and/or morphological changes of the cells, but preserves the surface components of the cells in a state in which at least a portion thereof are still available for binding to analyte ligands. Fixing of the cells also makes it less likely that adhered cells are able to dissociate from the sensing surface during subsequent analyses. As mentioned in relation to the first aspect, this is a particular advantage in embodiments in which the sensor is provided with, or forms part of a flow cell. Fixing of the cells also increased the rigidity of the cell layer, which may improve the sensitivity of the chemical sensor, as discussed in more detail below.

Before rendering the cells inactive, an optional step of microscopy may be used to check the layout and density of the cells on the sensor surface. Various microscopy approaches may be used, although fluorescence microscopy may be mentioned, in which case incubation of the adhered and/or fixed cells with a fluorescent dye (e.g. a nuclear dye) is undertaken before microscopy. If an appropriate cell count and/or density has not been achieved, further growth of the cells may then be allowed before inactivation. Microscopic monitoring of the sensing surface may be undertaken at any or all stages of the method to ascertain the progress of formation of the cell layer. Microscopy may also be used after the inactivation step, and after the optional step of fixing the cells.

Following adhesion and rendering of the cells inactive, the sensing surface is preferably treated with an acidic solution to remove non-adhered cellular and non-cellular material. This acidic solution, which may have a pH less than 5, preferably less than 3, and in some instances approximately 1, may also contain a low molecular weight salt. It may also contain an appropriate buffer, such as glycine.

In certain embodiments of the sensor and method of the invention, the sensor is an acoustic wave device. Such a device may, in particular embodiments, be a piezoelectric sensor, or quartz crystal microbalance.

Where the sensor is a QCM, the sensor may be housed in a sensor element having a removable cover which allows access to the sensor surface without needing to remove the sensor/QCM crystal from the housing. Such a sensor element arrangement is described in WO 2008/132487.

In a related, third aspect, the present invention provides a method of detecting an interaction between an analyte ligand and a cell, the method comprising the steps of providing a mass-sensitive chemical sensor according to the first aspect or obtained according to the method of the second aspect and having inactive cells adhered to or near a sensing surface thereof; introducing the analyte ligand into the vicinity of the sensing surface so as to allow interaction between analyte ligand and cells; and, where an interaction is present, detecting the interaction by means of the change in mass at the sensing surface due to binding of analyte ligand to the cells.

In embodiments of the third aspect of the invention, the sensor surface is stabilised prior to analyte introduction by bringing it into contact with the intended running buffer for the interaction detection. This stabilisation may take place for several hours. In certain embodiments, the analyte ligand is diluted using running buffer solution which has previously been used to stabilise the sensor. In embodiments in which the sensor is provided with, or forms part of, a flow cell, running buffer may be taken from the outlet of the flow cell and used to dilute a sample of analyte prior to introduction of the latter into the flow cell. In preferred embodiments, the running buffer is taken from the outlet and used to dilute the analyte essentially immediately before injection of the latter into the inlet of the flow cell. It will be appreciated that running buffer for use according to this step can only be obtained during periods when no analyte is present in the flow cell.

By using running buffer which has previously been used to stabilise the sensor surface, an improved matching between the analyte buffer and the running buffer may be achieved. This helps to reduce signal artifacts due to changes in buffer characteristics when the analyte is introduced. In preferred embodiments, control analyses are also carried out, in which running buffer from the stabilisation step is re-introduced to the sensor, but without inclusion of the analyte.

In certain embodiments, the binding interaction between analyte ligand and cells is detected at a plurality of different concentrations of analyte ligand. Such an approach allows the determination of kinetic parameters for the binding interaction between analyte and cell. The determination of kinetic parameters from data collected at multiple concentrations of analyte may be achieved using, for example, the approaches described by Myszka (*J. Molec. Recognit.,* 1999, 12, 279) or Morton and Myszka (*Methods Enzymol.,* 1998, 295, 268-294).

In a fourth aspect, the present invention provides a mass-sensitive chemical sensor obtainable by the method of the second aspect, the chemical sensor being suitable for detection of an interaction between an analyte ligand and the adhered, inactive cells by means of the change in mass at the sensor surface due to binding of analyte ligand to the cells. The sensor of the fourth aspect is preferably provided with, or forms part of, a flow cell.

It will be appreciated that the sensor of the fourth aspect may be used in a method of the third aspect. Compared to prior art sensors having cells adhered at or near their sensing surfaces, the sensor of the fourth aspect has the advantage that the cells are inactive and hence the sensor is capable of providing an accurate signal representative of the binding interaction per se. In a fifth aspect, the present invention provides the use of a mass-sensitive chemical sensor for analysing the binding interaction between an analyte ligand and a cell immobilised on or near a sensor surface of the chemical sensor.

Unlike prior art approaches, the fifth aspect is concerned with analysing the binding interaction per se between analyte and cell. In the prior art, those studies involving immobilised cells use the sensors for analysing the post-binding morphological and other changes which occur in the cells.

In preferred embodiments of the fifth aspect, the cells are inactive. In certain embodiments, the cells are fixed. Fixation approaches are described above in relation to the first aspect of the invention. In certain embodiments, the binding interaction is quantified; in particular the binding interaction between analyte ligand and cells may be detected at one specific concentration of analyte ligand, or preferably at a plurality of different concentrations of analyte ligand. Such approaches allow the determination of kinetic parameters for the binding interaction between analyte and cell, as described above.

In a sixth aspect, the invention provides a method of improving the sensitivity and/or sensing range of a mass-sensitive chemical sensor comprising an acoustic wave device, such as a quartz crystal microbalance, and having cells immobilised on or near a sensor surface thereof, the method comprising the step of fixing the cells or embedding the cells within a cross-linked polymeric matrix.

In certain embodiments, the cells are inactive (e.g. fixed). In addition or alternatively, the sensor may be provided with, or form part of, a flow cell.

Acoustic sensors have a limited decay length which determines the sensing distance from the sensing surface. Eukaryotic cells with sizes in the 10 μm range may not be completely sensed by the piezoelectric sensor. However, the inventors have found that the sensing range from the surface can be extended if the cell layer is sufficiently rigid. In the present invention, the fixing of the cells (e.g. with a cross-linking agent, as described above), or the embedding of the cells within a cross-linked polymeric matrix, provides rigidity to the cell layer on the sensing surface. This is likely to extend the sensing range of the acoustic sensor in the cell layer and consequently increase the sensitivity of the sensor.

If a cross-linked polymeric matrix is used for the sixth aspect, this may be selected from a range of matrices known from the biosensor field, for example, polysaccharide based matrices. The appropriate ratio of cells:polymeric matrix components may readily be determined by routine experimentation. It will be appreciated that a certain minimum density of cells needs to be accessible to the analyte ligand at the surface of the matrix distal to the sensing surface in order to provide a reliable sensing response.

In a seventh aspect, the invention provides a method of improving the sensitivity and/or sensing range of a mass-sensitive chemical sensor based on an acoustic wave device, such as a quartz crystal microbalance, the method comprising immobilising polymeric particles on or near a sensor surface thereof.

The polymeric particles (consisting of cross-linked polymer and being in the form of e.g. beads, such as polysaccharide beads, such as agarose) of the seventh aspect may be used in an analogous manner to the fixed or embedded cells of the sixth aspect. The particles may be attached to the sensing surface using conventional methods (e.g. using organic coupling chemistry standard in the biosensor field, such as EDC/NHS coupling). Molecules of interest (receptors, ligands, enzymes, lectins etc.) for chemical sensing studies may be attached to the beads, either before or, more preferably, after attachment of the beads to the sensing surface (again using conventional organic coupling techniques), such that the sensing surface presents a rigid layer of such molecules. As in the sixth aspect, the sensing range from the surface of a sensor prepared according to the seventh aspect is extended, and the sensitivity thereof is enhanced.

When a layer of cells is fixed or embedded in the method of the sixth aspect, an additional step may be undertaken of attaching a layer of further chemical species of interest to the cell layer. The so-formed layer of further chemical species (e.g. receptors, receptor ligands, lectins, sugars etc.) may then be used in chemical sensing studies, with the beneficial effects of the rigid cell layer being gained.

In an eighth aspect, the present invention also provides a mass-sensitive chemical sensor obtainable according to the method of the seventh aspect.

In a ninth aspect, the present invention provides a method of enhancing the signal to noise ratio in a mass-sensitive chemical sensor, the method comprising the step of using running buffer solution which has previously been used to stabilise the sensor to dilute a sample of analyte prior to introduction of the latter to the sensing surface.

The advantage of the ninth aspect is described above in connection with the third aspect. In a preferred embodiment, the mass-sensitive chemical sensor is provided with, or forms part of, a flow cell, and the method comprises the step of using running buffer from the outlet of the flow cell to dilute a sample of analyte prior to injection of the latter into the flow cell.

The present invention will now be described in more detail by way of example only and with reference to the appended drawings

DETAILED DESCRIPTION

Example 1

General Protocol

The present invention provides a method which aims, ultimately, to allow determination of kinetic and affinity data between cells and proteins or other biologically relevant molecules such as drugs, antibodies or receptors. While interaction affinities and rates have previously been determined for cell surface receptors and their receptors/binders as isolated proteins, it has not been done on actual cells. In striving for more biologically relevant assays for e.g. pharmaceutical development, real-time interaction assays with whole eukaryotic cells should constitute a major step forward. Here, a method has been developed for real-time interaction studies of eukaryotic cells and their interacting partners. An exemplary protocol comprises the steps of 1. Spin coating of a polystyrene surface onto a sensor
2. UV treatment of polystyrene surface
3. Growing cells on sensor surface
4. Fixing cells on sensor surface
5. Optional pretreatment of sensor surface with glycine
6. Stabilisation of the sensor surface in the biosensor instrument
7. Injection of ligands/analyte to determine kinetics and affinity of binding Biosensor analysis of immobilised whole cells provides several difficulties that need to be overcome. First, the significantly more complex surface that a surface with immobilised eukaryotic cells constitutes requires robust procedures for stabilisation of the cell surface in the sensor system since the expected signal level will be low and significant signal drift would make determination of interaction constants difficult. Step 4 of this exemplary method facilitates a stable surface of cells that are firmly attached to the sensor surface, and which does not dissociate. Steps 5 and 6 provide the necessary stabilisation of the sensor surface in the system to accomplish a significantly low drift to carry out the assay.

Secondly, the acoustic sensor has a limited decay length which determines the sensing distance from the sensing surface out in the liquid. Eukaryotic cells with sizes in the 10 µm range are likely not completely sensed by the piezoelectric sensor. However, experiments have shown that the sensing range from the surface can be extended if the added layer is sufficiently rigid. In the present invention, the fixing of the cells with a cross-linking agent according to step 4 provides rigidification of the cells on the sensing surface which is likely to extend the sensing range of the acoustic sensor in the cell layer and consequently increase the sensitivity.

Third, with a low expected signal level for the interaction studies of the cell surface due to the limited sensing distance and due to the relatively low concentration of surface receptors normally present on eukaryotic cells, the elimination of unwanted experimental side effects such as signal contribution from buffer matrix (buffer effects) is necessary. This is accomplished by, for instance, exact matching of the sample buffer as described in step 7 of this exemplary method.

Detailed Description of the Method Steps

1. Spin Coating of a Polystyrene Surface onto a Sensor

Prior to spin coating, conductivity-checked (Smart Tweezers, Siborg Systems Inc.) unpolished QCM crystals undergo oxygen plasma treatment (Electronic Diener, Femto), followed by sonication in ethanol in order to ensure appropriate cleaning of the crystal surface. Polystyrene coating of the crystal was performed by spin coating. Briefly, 10 µl of polystyrene solution, previously prepared to a concentration of 5 mg/ml in toluene, was deposited in the center of the crystal and spin coated (Spin Coater®, model P6700 series, Specialty Coating Systems, INC.). An average of 56 Å+/−21 Å of polystyrene was coated on each crystal. The polystyrene coated crystals were subsequently stored at +4 deg C. prior to UV treatment.

2. UV Treatment of Polystyrene Surface

In order to enable optimised cell attachment and growth, oxidation of the polystyrene surface by UV irradiation is a preferred step. UV treatment was performed to ensure better wettability of the surface as measured by the contact angle of a water droplet with the polystyrene surface (The pocket Goniometer, PG-3, FIBRO System AB). The exposure time to UV was previously determined to obtain a contact angle of 60-65 degrees, in agreement with traditional tissue culture surfaces.

3. Growing Cells on Sensor Surface

Cells grown in appropriate media (depending on cell line) at 37 deg C. in a 5% $CO_2$ incubator were trypsinised (according to standard cell trypsination procedures) in order to prepare a single-cell suspension. Cell count was performed, using a hemocytometer, and cells were seeded on polystyrene surfaces to an appropriate density/concentration to reach about 70-80% coverage of the sensor surface after 24 hr incubation, as evaluated after fixation by nuclei staining (described in next paragraph).

4. Fixing Cells on Sensor Surface

After 24 hr incubation, the cells previously seeded on the crystals were subjected to fixation in formaldehyde (Sigma). The cell media was removed and cells were washed in ice-cold PBS. Fixation of the cells was subsequently performed by incubating the cells for 10 minutes at +4 deg C. with 0.5 ml of a 3.7% formaldehyde solution freshly prepared in ice-cold PBS. Three wash steps of 5 minutes were performed to remove the remaining formaldehyde. Subsequently nuclei stain was performed to evaluate the cell coverage of the crystal. Briefly, the cells were incubated for 3 min with the nuclei dye, DAPI (Invitrogen, $\lambda$Ex/Em: 358-461 nm) prepared to a final concentration of 2.8 $\mu$M. After a wash step in PBS cell-crystals were visualized under a fluorescent microscope (Nikon Eclipse 80i). Cell-crystals were then kept in PBS at +4 deg C.

5. Pretreatment of Sensor Surface with Glycine

Before being mounted into the chip holder and run into an Attana Cell 200 instrument (www.attana.com), cells undergo an optional pretreatment with a regeneration solution (glycine 10 mM, NaCl 500 mM, pH1). This treatment further cleans up the surface hence enabling a quicker stabilization of the cell-crystal as well as a more stable baseline in the Attana Cell 200 instrument.

6. Stabilisation of the Sensor Surface in Biosensor Instrument

Pretreated cell-crystals were mounted in the Attana Cell 200 instrument chip holder and inserted into the instrument to stabilise, for several hours or overnight at 25-50 $\mu$l/min in PBS supplemented with 0.025% of Tween (PBST). The run, evaluation of lectins and/or antibodies binding, were performed at 25 $\mu$l/min at 20 deg C.

7. Injection of Ligands/Analyte to Determine Kinetics and Affinity of Binding

The assay is designed to characterize the mechanisms of molecular interaction of ligand analytes, e.g. antibodies or lectins, directed towards cell receptors or other specific components, e.g. carbohydrate structures, at the cell surface through determination of affinity constants. The aim is to provide a biophysical interpretation of interactions occurring at the surface of fixed cells, e.g. human cancerous adherent cells. The quality of the evaluation of binding constant in a biomolecular binding reaction depends on the conditions at which assays are performed. Affinity and rate constants can be determined by monitoring the binding interaction at one particular concentration of analyte, or at a plurality of different concentrations of analyte, optionally with intermediate regeneration of the cell surface between analyte injections (this may be achieved using glycine 10 mM at pH 1 supplemented with NaCl 0.5M).

In the Example reported herein, cell-crystals covered with 70-80% cells, flow rate (25 $\mu$l/ml), running buffer (PBST) and contact time between 80-170 seconds were used to maximize the response as well as to minimize non specific interactions, lower mass transport effect and dispersion. To provide robust and accurate determination of kinetics and affinity constants a set of concentrations can be used, and in a typical embodiment the set involves between 3 and 5 different concentrations which are repeated at least twice. The range of concentration should be at least 10 fold and at the highest concentration the analyte should be bound to at least half of the available surface receptors. Appropriate concentrations of analyte molecules are dependent on the affinity of analyte for the receptor. For an antibody of affinity 1 nM a range of 3-50 $\mu$g/ml was found appropriate and for 15 nM affinity lectins a concentration range up to 100 $\mu$g/ml was needed to achieve maximal response (typically 5-10 Hz for antibodies to cell surface receptors and 250 Hz for lectins binding to cell surface carbohydrates).

With small expected signal responses and with highly complex sensor surfaces matching of the running buffer with the sample buffer becomes highly preferred. In an optional approach to provide optimal matching between sample buffer and the running buffer that flows over the sensor surface, the buffer that has passed the sensor surface is collected from the outlet and reused for sample dilution. Preferably, the buffer is collected just prior to the sample injection to provide best possible matching between buffers. Optionally, control injections are carried out in the same manner, but without the addition of any analyte. Buffer controls can then be used to eliminate artifacts and provide valid high quality biosensor analysis.

Kinetic analysis was performed similarly to conventional interaction assay with determination of on/off rate and affinity constant (Kd) (see Myszka references above).

Example 2a

Cell-Lectin Interaction on an Attana Cell 200 Instrument

Figure 1:
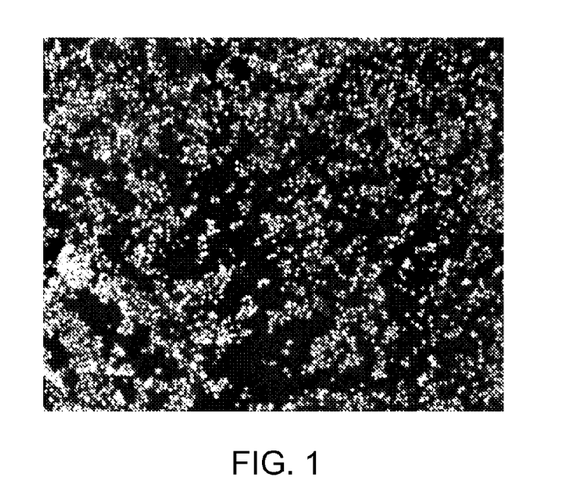
FIG. 1 is a fluorescence micrograph of a QCM sensor having human breast carcinoma cells fixed thereon.

MDAMB468 cells (human breast carcinoma cell line) were seeded onto a UV-treated PS crystal, fixed after 24 H in 3.7% formaldehyde and nuclei stained as shown in FIG. 1.

Figure 2:
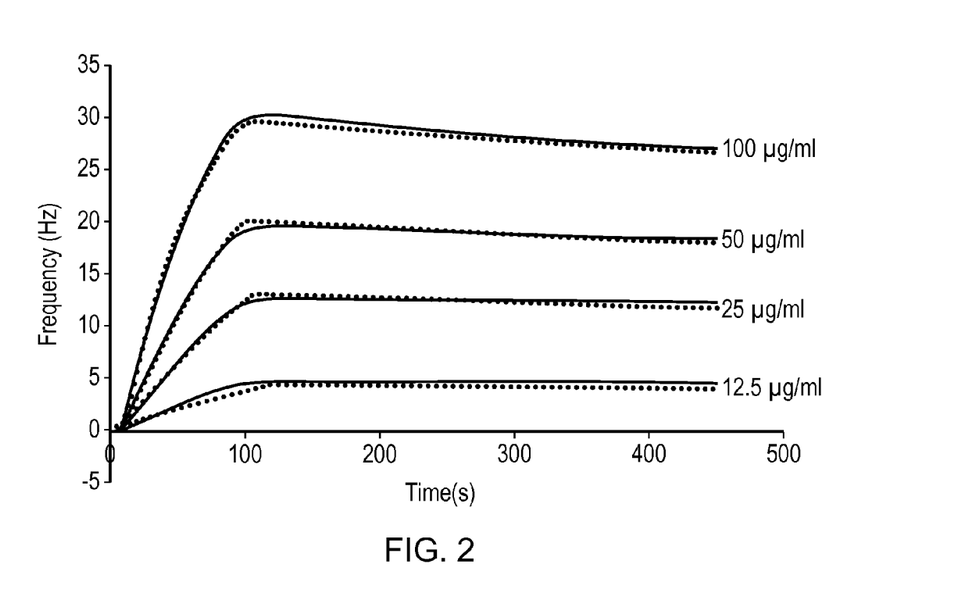
FIG. 2 shows data from a series of concanavalin A (ConA) binding experiments conducted using a QCM sensor according to FIG. 1. Con A was injected at 12.5 µg/ml, 25 µg/ml, 50 µg/ml, 100 µg/ml with the respective responses in increasing order. The affinity was determined to 15 nM.
Figure 3:
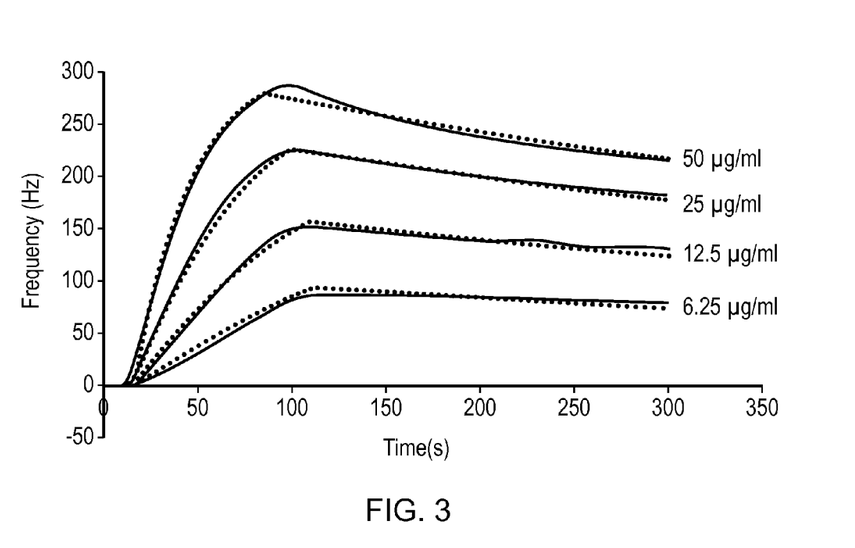
FIG. 3 shows data from a series of wheat germ agglutinin (WGA) binding experiments conducted using a QCM sensor according to FIG. 1. WGA was injected at 6.5 µg/ml, 12.5 µg/ml, 25 µg/ml, 50 µg/ml, with the respective responses in increasing order. The affinity was determined to 93 nM.

The experiment was performed at 20 deg C. under a flow rate of 25 $\mu$l/min. PBS supplemented with 0.025% Tween was used as running buffer. Various concentrations of lectins (conA and WGA) were injected over the cells with a contact time of 85 seconds and dissociation was monitored for at least 300 seconds. The data is shown in FIGS. 2 and 3. Kinetics evaluation was performed using the software Clamp (*TIBS*, 1998, 23, 149).

The two lectins, Con A and WGA bear different structures and sugar specificity. The experiment presented here shows that both lectins interact with carbohydrates at the surface of the cells with different intensity and affinity, hence providing valuable information regarding the glycan composition of the glycoconjugates of the MDAMB468 cell surface. The affinity constants for the interaction between the cell surface carbohydrates and the two lectins were 15 nM and 93 nM for Con A and WGA, respectively.

Example 2b

Specificity of the Lectin-Cell Surface Interaction

Figure 10:
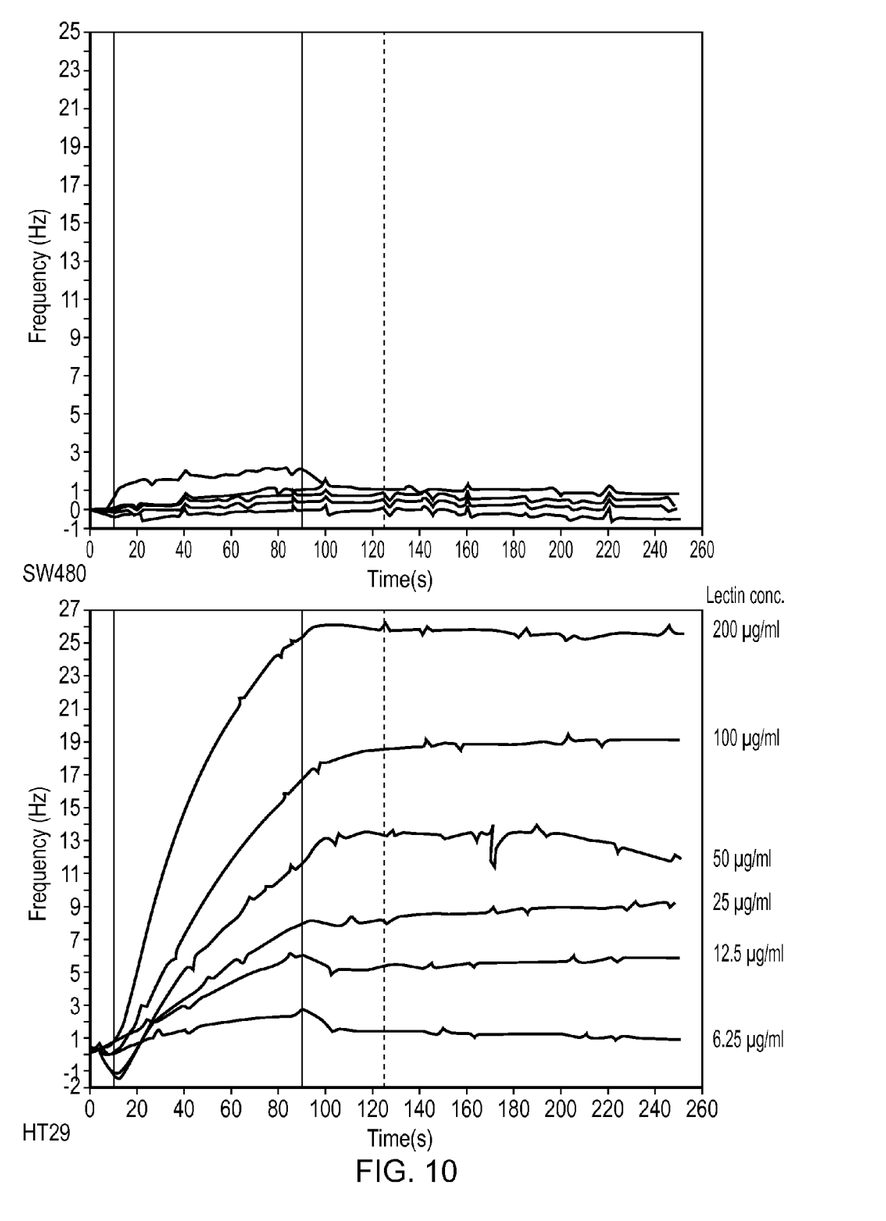
FIG. 10 shows data obtained from interactions between a GalNAc binding lectin and two different cell lines, exposing different glycotopes on their respective cell surfaces.

To further verify the specificity of the lectin-cell surface carbohydrate interaction, a GalNAc binding lectin was allowed to interact at different concentrations with two different cell lines, SW480 and HT29, exposing different glycotopes on their respective surfaces. The lectin was prepared in running buffer at concentrations ranging from 6.25 $\mu$g/ml to 200 and subsequently injected over SW480 and HT29 cells on respective sensor surfaces. The lectin was injected for 85 sec and was thereafter allowed to dissociate for 200 sec. As shown in FIG. 10, only minor binding was detected on SW480 cells, whereas the binding to HT29 cells was concentration dependent and significantly greater.

Example 3

Cell Antibody Interaction on an Attana Cell 200 Instrument

Figure 4:
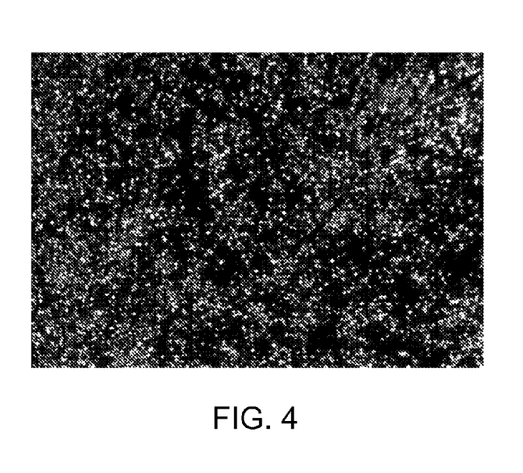
FIG. 4 is a fluorescence micrograph of a QCM sensor having human epidermoid carcinoma (A-431) cells fixed thereon.

A-431 cell line is a human epithelial adherent cell line (epidermal carcinoma), over-expressing the EGFR receptors Fixed and DAPI stained A-431 cells on UV treated polystyrene QCM crystal are shown in FIG. 4.

The crystal was pretreated in 10 mM glycine, 500 mM NaCl, pH 1 at room temperature for 20 min and washed in PBS-T before mounting into the chip holder. The crystal was stabilized at 20 deg C. and a flow rate of 40 µl/min, PBS-T (0.025% Tween) overnight. Flow rate was reduced to 25 µl/min during antibody injections.

Antibody: anti-EGFR sc 101 in PBS 2 mg/ml (Santa Cruz). 3 different antibody concentrations, 25, 12.5 and 6 µg/ml were tested.

Figure 5:
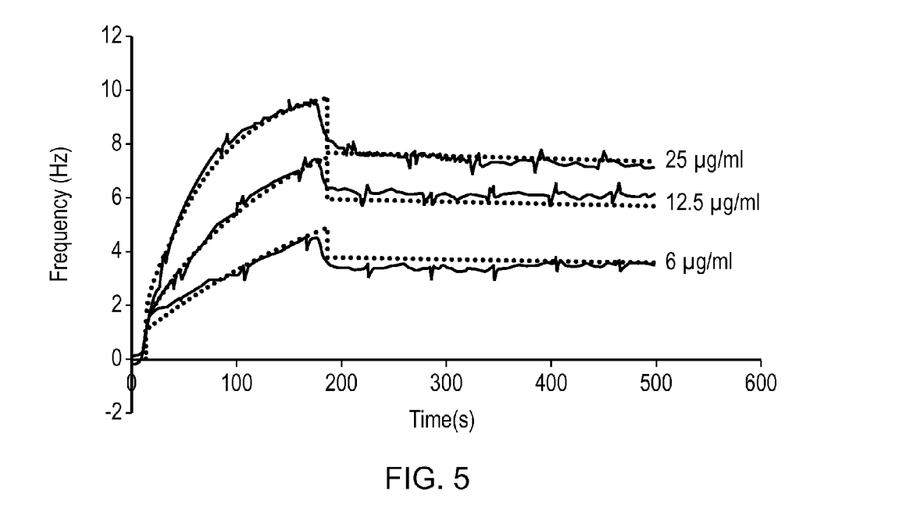
FIG. 5 shows data obtained from a series of binding experiments conducted using the QCM sensor of FIG. 4 and an anti-EGFR antibody. The antibody was injected at 6, 12.5 and 25 µg/ml with the respective responses in increasing order. The affinity was determined to 1.2 nM.

The analytical results are shown in FIG. 5. Kinetic rate and affinity constants (Kd=1.2 nM) for the interaction between the anti-EGFR and the cell surface EGFR receptors were determined.

Example 4

Figure 6A:
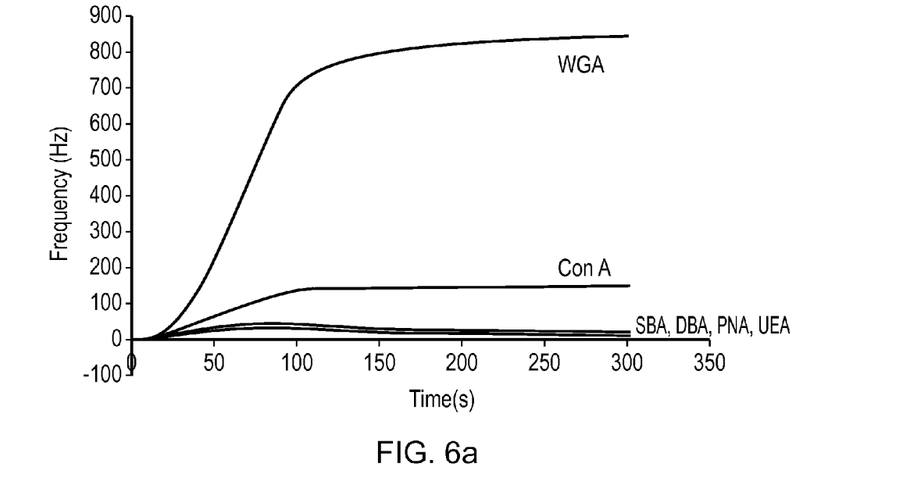
FIG. 6 illustrates data obtained from the screening of a series of lectins for binding to a QCM sensor having A-431 cells fixed thereon (a), and equivalent experiments in which no cells were present (b).
Figure 6B:
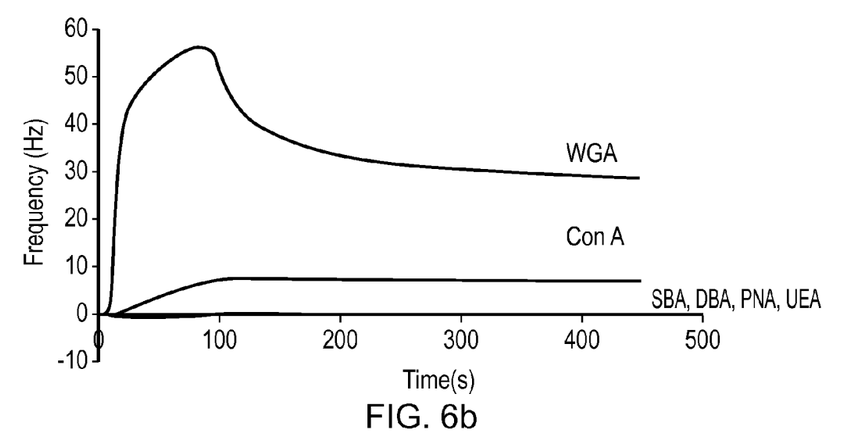

Cell-Lectin Interaction on an Attana Cell 200 Instrument—Sensitivity Improvement by Cell Fixation A-431 cells (human epithelial carcinoma cell line) were seeded onto UV-treated PS crystal and fixed after 24 H in 3.7% formaldehyde. The experiment were performed at 20 deg C. under a flow rate of 25 µl/min in PBS supplemented with 0.025% Tween. The lectins WGA and ConA were injected over the cells at a concentration of 50 µg/ml for a contact time of 85 sec and dissociation was monitored for 215 sec. A control crystal consisting of UV-treated PS crystal devoid of cells, but otherwise identically treated and prepared, was included in the experiment to evaluate the contribution of non lectin-cell interactions. Screening experiments were conducted under the same conditions with a variety of other lectins to show the specificity of the ConA and WGA interactions (FIG. 6a, with A-431 cells present, and FIG. 6b, with no cells present).

Figure 7A:
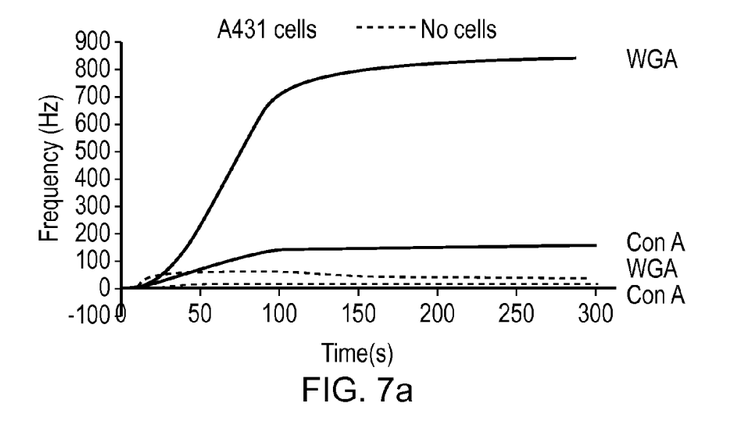
FIGS. 7a and 7b show a comparison between ConA and WGA binding to a QCM sensor with and without fixed A-431 cells.
Figure 7B:
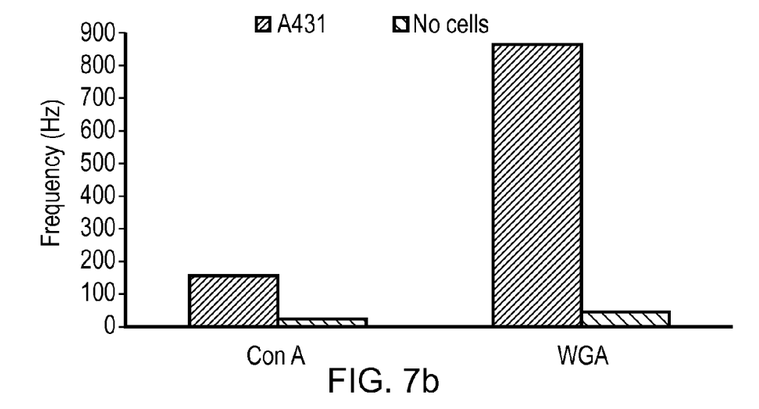

The high binding response of WGA (>800 Hz) to the A-431 cell surface (FIG. 7a) shows a significant increase in response compared to the expected response of a two dimensional surface containing the same, or higher, surface density of relevant carbohydrates. The expected maximum response that can be achieved on a two dimensional surface should be in the range of 100 Hz provided a molecular weight for WGA of 35000 Da, since there is a practical limit of molecular packing density on the surface. The approximate 8 fold increase in sensitivity can be explained by the surface enhancement that the fixed cells immobilised on the surface provide. While the cells have a thickness in the range of 10 µm and the QCM sensor normally has a decay length in the range of a few hundred nm, the improvement in sensitivity due to surface enhancement should be limited, if it were not for the rigidification of the cells that the fixation provides. Consequently, the provided data shows that sensitivity and dynamic range of the sensor can be improved by addition and fixation of cells to the surface. FIG. 7b directly compares the A-431 and control crystal frequency shifts for ConA and WGA binding.

Example 5

Surfaces and Fixation Methods

A-431 cells were immobilized on gold or polystyrene (PS) surfaces. Immobilized cells were subsequently fixed according to two different approaches. Fixation strategies are generally divided into additive fixation, based on the formation of covalent bonds between proteins, and denaturing fixation which consists of a dehydration of the various cell constituents. In this experiment fixation methods based on each of these two principles were tested. A microscopic evaluation of nuclei stained cells was performed to evaluate the extent of the immobilization.

The four conditions tested were as follow:
A-431 immobilized on polystyrene and fixed with Formaldehyde+Methanol (PSFM)
A-431 immobilized on polystyrene and fixed with Formaldehyde (PSF)
A-431 immobilized on gold and fixed with Formaldehyde+Methanol (GoldFM)
A-431 immobilized on gold and fixed with Formaldehyde (GoldF)

The binding of the lectin Con A to A-431 was used to evaluate the gold surface as an alternative for hosting mammalian cells, in addition to the previously described polystyrene surface. Also, a denaturing fixation method using formaldehyde and methanol was compared to the additive fixation strategy based on formaldehyde previously described.

Figure 8:
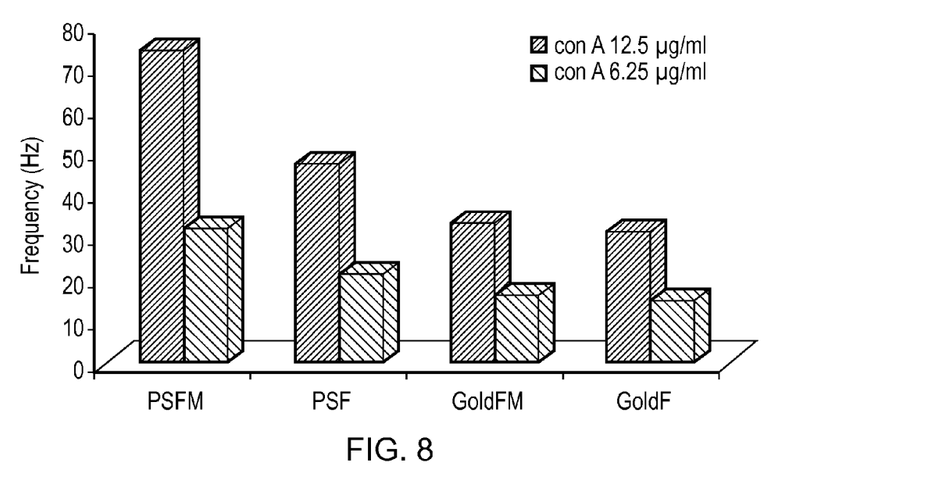
FIG. 8 shows the results of an experiment studying Con A binding to A-431 cells immobilized on either gold or polystyrene (PS) surfaces. For each of the surfaces, two fixation methods were used; formaldehyde (F) or formaldehyde+methanol (FM). The chart compiles the maximal frequencies recorded by the Attana Cell 200 instrument as a result of the binding of Con A at 12.5 µg/ml and 6.25 µg/ml to A-431 cells for the four conditions PSFM, PSF, GoldFM and GoldF.
Figure 9:
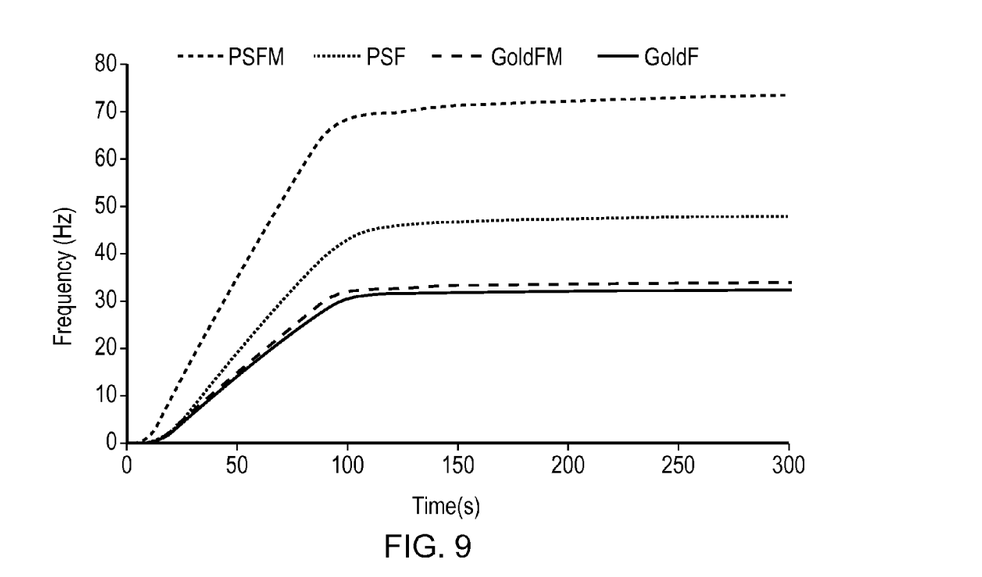
FIG. 9 shows the time-dependent frequency changes upon binding and release of Con A to A-431 cells. The interaction was evaluated in the four conditions employed in the experiment described in FIG. 8, i.e. PSFM, PSF, GoldFM, GoldF.

It appears clear from FIGS. 8 and 9 that PS is a better substrate for cell attachment, with the highest signal obtained with denaturing fixation; however a gold surface may be used as an alternative. Similarly although both fixation approaches may be used, denaturing fixation appears advantageous in this particular example.

The optimal choice of fixation method, as well as surface type, are dependent upon the system to be studied. These examples show that not only both additive and denaturing fixation methods, but also either gold or polystyrene surfaces, are conditions compatible with high quality measurement using the Attana Cell 200 instrument.

The foregoing Examples are intended to illustrate specific embodiments of the present invention and are not intended to limit the scope thereof, the scope being defined by the appended claims. All documents cited herein are incorporated herein by reference in their entirety.

The invention claimed is:

1. A mass-sensitive chemical sensor having a sensing surface, comprising inactive cells adhered to the sensing surface and a flow cell, wherein the mass-sensitive chemical sensor is provided with, or forms part of, the flow cell, whereby the mass-sensitive chemical sensor is suitable for detection of an interaction between an analyte ligand and the adhered, inactive cells by a change in mass at the sensor surface due to binding of analyte ligand to the cells.

2. The mass-sensitive chemical sensor of claim 1, wherein the inactive cells adhered to the sensing surface are fixed to the sensing surface.

3. The mass-sensitive chemical sensor of claim 1, wherein the inactive cells are eukaryotic.

4. The mass-sensitive chemical sensor of claim 1, wherein the sensing surface is provided with a polymeric coating.

5. The mass-sensitive chemical sensor of claim 1, wherein the sensing surface, prior to cell immobilisation, has a contact angle selected from the group consisting of 10 to 90 degrees, 20 to 80 degrees, and 30 to 70 degrees, measured using high purity water.

6. The mass-sensitive chemical sensor of claim 5, wherein the sensing surface, prior to cell immobilisation, has a contact angle 20 to 80 degrees measured using high purity water.

7. The mass-sensitive chemical sensor of claim 6, wherein the sensing surface, prior to cell immobilisation, has a contact angle of 30 to 70 degrees, measured using high purity water.

8. The mass-sensitive chemical sensor of claim 1, wherein the mass-sensitive chemical sensor is an acoustic wave device.

\* \* \* \* \*